(12) United States Patent  
Kovach

(10) Patent No.: US 10,105,219 B2  
(45) Date of Patent: Oct. 23, 2018

(54) MITRAL VALVE LEAFLET CLIP

(71) Applicant: St. Jude Medical, Cardiology Division, Inc., St. Paul, MN (US)

(72) Inventor: Melinda K. Kovach, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 751 days.

(21) Appl. No.: 13/782,008

(22) Filed: Mar. 1, 2013

(65) Prior Publication Data

US 2014/0039607 A1 Feb. 6, 2014

Related U.S. Application Data

(60) Provisional application No. 61/678,850, filed on Aug. 2, 2012.

(51) Int. Cl.
*A61F 2/24* (2006.01)
*A61B 17/12* (2006.01)
(Continued)

(52) U.S. Cl.
CPC ........ *A61F 2/2427* (2013.01); *A61B 17/0467* (2013.01); *A61B 17/0487* (2013.01);
(Continued)

(58) Field of Classification Search
CPC ............... A61F 2/2427; A61B 17/0401; A61B 17/0482; A61B 2017/0454;
(Continued)

(56) References Cited

U.S. PATENT DOCUMENTS 5,041,129 A * 8/1991 Hayhurst ........... A61B 17/0401  
606/139  
5,156,608 A 10/1992 Troidl et al.  
(Continued)

FOREIGN PATENT DOCUMENTS

AU 2002300522 B2 1/2007  
WO 9620749 A1 7/1996  
(Continued)

OTHER PUBLICATIONS

International Search Report and Written Opinion for Application No. PCT/US2013/065360 dated Apr. 23, 2014.  
(Continued)

*Primary Examiner* — Katherine M Shi  
*Assistant Examiner* — Michael Mendoza  
(74) *Attorney, Agent, or Firm* — Lerner, David, Littenberg, Krumholz & Mentlik, LLP

(57) ABSTRACT

A device for gathering tissue of a heart valve leaflet may include an outer tube extending in an elongation direction and having an open distal end, a capture tool movable in the outer tube between a contained position and a use position, and a tissue securing component disposed at a distal end of the outer tube and adapted to be applied to captured tissue of the heart valve leaflet to hold the captured tissue in a gathered configuration. The outer tube may have an inner surface and a lumen extending therethrough. The capture tool may be operable to capture tissue of the heart valve leaflet and to draw the captured tissue into the outer tube in the gathered configuration. The tissue securing component may be a suture having a looped portion. At least part of the looped portion may extend through a lumen of at least one support tube.

23 Claims, 3 Drawing Sheets

(51) Int. Cl.
  *A61B 17/06* (2006.01)
  *A61B 17/00* (2006.01)
  *A61B 17/04* (2006.01)

(52) U.S. Cl.
  CPC ........ *A61B 17/12013* (2013.01); *A61B 17/06* (2013.01); *A61B 2017/00004* (2013.01); *A61B 2017/00243* (2013.01); *A61B 2017/00783* (2013.01); *A61B 2017/0417* (2013.01); *A61B 2017/0488* (2013.01)

(58) Field of Classification Search
  CPC ............ A61B 17/0467; A61B 17/0487; A61B 17/12013; A61B 2017/0488; A61B 17/06; A61B 2017/00004; A61B 2017/00783; A61B 2017/0417; A61B 2017/00243
  See application file for complete search history.

(56) References Cited

U.S. PATENT DOCUMENTS

| | | | |
|---|---|---|---|
| 5,499,991 | A | 3/1996 | Garman et al. |
| 5,601,573 | A | 2/1997 | Fogelberg et al. |
| 5,741,278 | A | 4/1998 | Stevens |
| 5,749,879 | A | 5/1998 | Middleman et al. |
| 5,921,993 | A | 7/1999 | Yoon |
| 6,258,105 | B1 | 7/2001 | Hart et al. |
| 6,440,152 | B1 | 8/2002 | Gainor et al. |
| 6,569,182 | B1 | 5/2003 | Balceta et al. |
| 6,626,930 | B1 * | 9/2003 | Allen ............. A61B 17/0401 606/213 |
| 6,752,813 | B2 | 6/2004 | Goldfarb et al. |
| 6,945,978 | B1 | 9/2005 | Hyde |
| 7,011,669 | B2 | 3/2006 | Kimblad |
| 7,464,712 | B2 | 12/2008 | Oz et al. |
| 7,569,062 | B1 | 8/2009 | Kuehn et al. |
| 7,758,595 | B2 | 7/2010 | Allen et al. |
| 8,777,966 | B2 | 7/2014 | Dale et al. |
| 8,951,285 | B2 * | 2/2015 | Sugimoto ........ A61B 17/00234 606/232 |
| 2001/0016750 | A1 | 8/2001 | Malecki et al. |
| 2002/0010388 | A1 | 1/2002 | Taylor et al. |
| 2002/0013571 | A1 | 1/2002 | Goldfarb et al. |
| 2002/0035390 | A1 | 3/2002 | Schaldach et al. |
| 2002/0049457 | A1 | 4/2002 | Kaplan et al. |
| 2002/0107531 | A1 | 8/2002 | Schreck et al. |
| 2002/0183768 | A1 | 12/2002 | Deem et al. |
| 2003/0065335 | A1 | 4/2003 | Guido et al. |
| 2003/0093071 | A1 | 5/2003 | Hauck et al. |
| 2003/0120264 | A1 | 6/2003 | Lattouf |
| 2004/0030335 | A1 | 2/2004 | Zenati et al. |
| 2004/0039442 | A1 | 2/2004 | St. Goar et al. |
| 2004/0087985 | A1 | 5/2004 | Loshakove et al. |
| 2004/0176784 | A1 | 9/2004 | Okada |
| 2004/0181238 | A1 | 9/2004 | Zarbatany et al. |
| 2004/0193185 | A1 | 9/2004 | McBrayer |
| 2004/0225183 | A1 * | 11/2004 | Michlitsch ......... A61B 1/00135 600/106 |
| 2005/0004583 | A1 | 1/2005 | Oz et al. |
| 2005/0090837 | A1 | 4/2005 | Sixto et al. |
| 2005/0096671 | A1 | 5/2005 | Wellman et al. |
| 2005/0107871 | A1 | 5/2005 | Realyvasquez et al. |
| 2005/0125011 | A1 | 6/2005 | Spence et al. |
| 2005/0143763 | A1 | 6/2005 | Ortiz et al. |
| 2005/0149072 | A1 | 7/2005 | DeVries et al. |
| 2005/0177176 | A1 | 8/2005 | Gerbi et al. |
| 2005/0251161 | A1 | 11/2005 | Saadat et al. |
| 2006/0009800 | A1 | 1/2006 | Christianson et al. |
| 2006/0089671 | A1 | 4/2006 | Goldfarb et al. |
| 2006/0122633 | A1 | 6/2006 | To et al. |
| 2006/0173422 | A1 | 8/2006 | Reydel et al. |
| 2006/0173473 | A1 | 8/2006 | Bob |
| 2007/0049952 | A1 | 3/2007 | Weiss |
| 2007/0093857 | A1 | 4/2007 | Rogers et al. |
| 2007/0102474 | A1 | 5/2007 | Shelton et al. |
| 2007/0102475 | A1 | 5/2007 | Ortiz et al. |
| 2007/0142846 | A1 | 6/2007 | Catanese et al. |
| 2007/0162056 | A1 | 7/2007 | Gerbi et al. |
| 2007/0197858 | A1 | 8/2007 | Goldfarb et al. |
| 2007/0198032 | A1 | 8/2007 | Ortiz |
| 2007/0225734 | A1 | 9/2007 | Bell et al. |
| 2008/0125796 | A1 | 5/2008 | Graham |
| 2008/0234705 | A1 | 9/2008 | Cropper et al. |
| 2008/0255427 | A1 | 10/2008 | Satake et al. |
| 2008/0294175 | A1 | 11/2008 | Bardsley et al. |
| 2008/0300624 | A1 | 12/2008 | Schwemberger et al. |
| 2008/0319455 | A1 | 12/2008 | Harris et al. |
| 2009/0062852 | A1 | 3/2009 | Marino |
| 2009/0118744 | A1 | 5/2009 | Wells et al. |
| 2009/0125038 | A1 | 5/2009 | Ewers et al. |
| 2009/0149870 | A1 | 6/2009 | Jugenheimer et al. |
| 2011/0054521 | A1 | 3/2011 | Ventura et al. |
| 2011/0077668 | A1 | 3/2011 | Gordon et al. |
| 2011/0087242 | A1 | 4/2011 | Pribanic et al. |
| 2011/0114700 | A1 | 5/2011 | Baxter, III et al. |
| 2011/0230897 | A1 | 9/2011 | Palermo et al. |
| 2011/0313432 | A1 | 12/2011 | Miles et al. |
| 2012/0022532 | A1 | 1/2012 | Garrison |
| 2012/0109159 | A1 | 5/2012 | Jordan et al. |
| 2012/0226291 | A1 | 9/2012 | Malizia et al. |
| 2013/0046332 | A1 | 2/2013 | Jones et al. |
| 2014/0039607 | A1 | 2/2014 | Kovach |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 2002000121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report for Application No. PCT/US2012/023437 dated Apr. 24, 2012.
International Preliminary Report on Patentability for Application No. PCT/US2012/023437 dated Aug. 6, 2013.
International Search Report and Written Opinion for Application No. PCT/US2013/023082 dated Oct. 1, 2013.
International Search Report and Written Opinion for Application No. PCT/US2013/024304 dated Jul. 5, 2013.
International Search Report and Written Opinion for Application No. PCT/US2013/052822 dated Jan. 21, 2014.
International Search Report and Written Opinion for Application No. PCT/US2013/052838 dated Oct. 11, 2013.
International Search Report and Written Opinion for Application No. PCT/US2013/052843 dated Oct. 11, 2013.
International Search Report for Application No. PCT/US2013/023077 dated May 14, 2013.
International Search Report for Application No. PCT/US2013/052832 dated Jan. 15, 2014.
Merriam-Webster definition of "fabric" as accessed on Dec. 17, 2014; http://www.merriam-webster.com/dictionary/fabric.

* cited by examiner

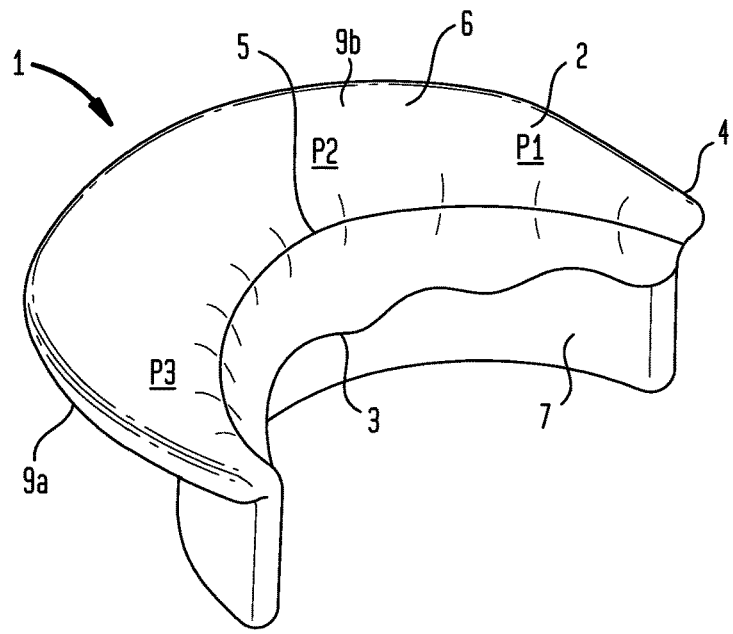
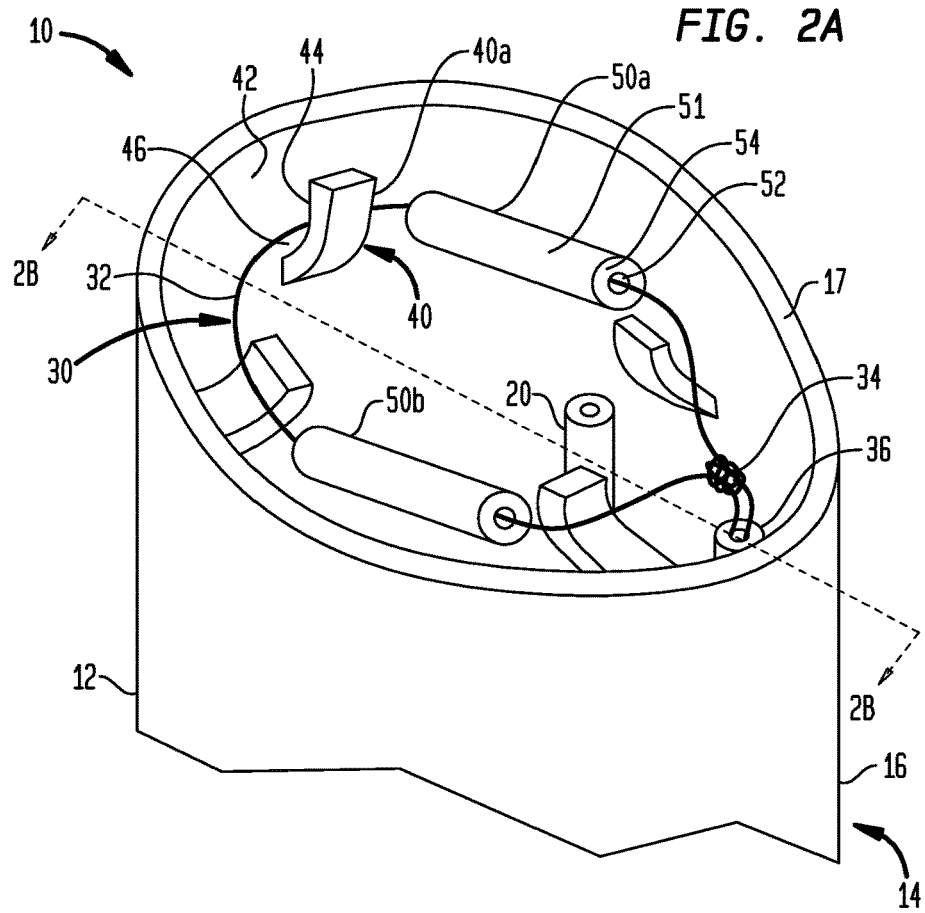

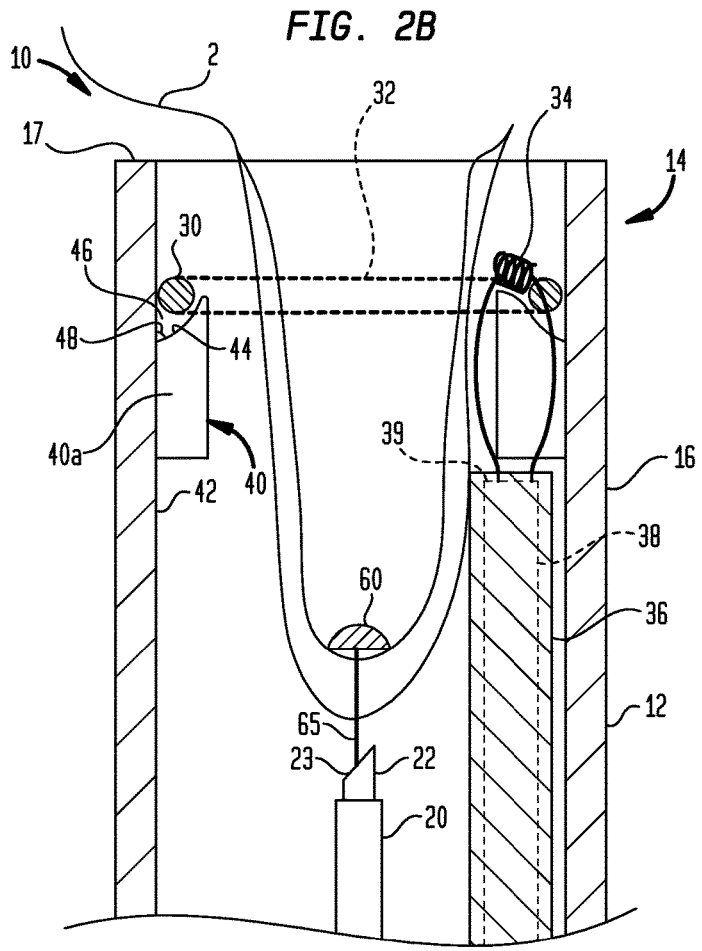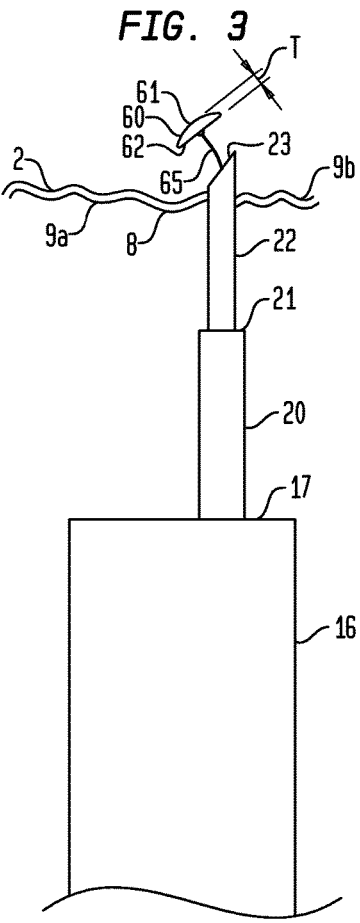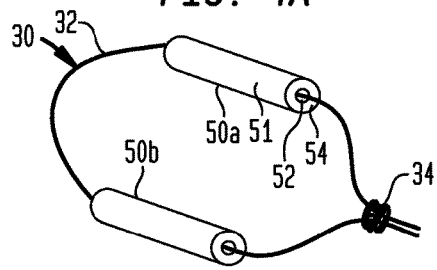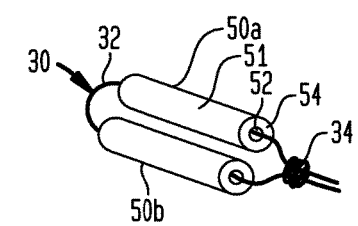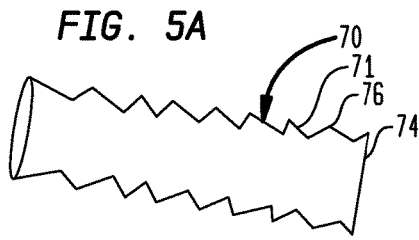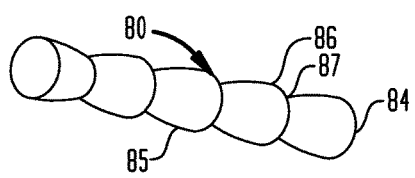

MITRAL VALVE LEAFLET CLIP

CROSS-REFERENCE TO RELATED APPLICATION

The present application claims the benefit of the filing date of U.S. Provisional Patent Application No. 61/678,850 filed Aug. 2, 2012, the disclosure of which is hereby incorporated herein by reference.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be broken. As a result, the valve does not close normally, and the unsupported valve leaflet may bulge back, or "prolapse," into the left atrium like a parachute. Thus, as the ventricle contracts, the abnormal leaflet may be propelled backwards, beyond its normal closure line into the left atrium, thereby allowing blood to flow back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

Devices and methods for gathering tissue of a heart valve leaflet are disclosed. A device for gathering tissue of a heart valve leaflet may include an outer tube extending in an elongation direction and having an open distal end, a capture tool movable in the outer tube between a contained position and a use position, and a tissue securing component disposed at a distal end of the outer tube and adapted to be applied to captured tissue of the heart valve leaflet to hold the captured tissue in a gathered configuration. The outer tube may have an inner surface and a lumen extending therethrough. The capture tool may be operable to capture tissue of the heart valve leaflet and to draw the captured tissue into the outer tube in the gathered configuration. The tissue securing component may be a suture having a looped portion. At least part of the looped portion may extend through a lumen of at least one support tube.

The at least one support tube may include first and second support tubes. At least part of the looped portion of the suture may extend through a lumen of each of the support tubes. The support tubes may be adapted to shape the captured tissue into a pleated configuration when the looped portion is tightened around the captured tissue. Each of the support tubes may have an outer surface having a smooth cylindrical shape. Each of the support tubes may have an outer surface that is roughened or knurled. Each of the support tubes may have an outer surface having serrations. Each support tube may have an outer surface that undulates in a longitudinal direction between opposed ends of the respective support tube. The support tube may consist essentially of one of a metal or a polymer. The support tube may have a central portion and end portions adjacent the central portion. The central portion may be weaker against bending than the end portions. The support tube may be adapted to shape the captured tissue into a pleated configuration when the looped portion is tightened around the captured tissue.

The looped portion of the suture may be adapted to move from an initial position to a tightened position. The support tubes in the initial position may have outer surfaces that are spaced apart from one another and disposed adjacent the inner surface of the outer tube. The outer surfaces of the support tubes in the tightened position may be disposed opposite one another adjacent the captured tissue. The inner surface of the outer tube may have a rib assembly extending therefrom. The rib assembly may form pockets adjacent the inner surface. The looped portion of the suture in the initial position may extend through the pockets of the rib assembly. The rib assembly may include a plurality of spaced apart ribs distributed circumferentially around the inner surface of the outer tube. The support tubes in the initial position may be disposed between adjacent ones of the spaced apart ribs. The rib assembly may include a single continuous rib extending circumferentially around the inner surface of the outer tube.

The looped portion of the suture may include a locking sliding knot configured to slide along the suture in only one direction. The device may also include a crimp configured to be tightened around the suture when the looped portion of the suture is in a tightened position holding the captured tissue in the gathered configuration. The device may also include a crimping apparatus adapted to clamp the crimp around two portions of the suture. The crimping apparatus may include a plunger disposed within a channel adjacent an inner surface of the outer tube. The channel may be partially defined by crimping members spaced apart from one another by a crimping slot having opposed surfaces spaced apart by a distance that is less than an initial width of the crimp. The capture tool may include a needle element and a securing element. The needle element may be operable to penetrate tissue of the heart valve leaflet. The securing element may have a proximal surface adapted to capture tissue of the heart valve leaflet. The securing element may include a resorbable anchor and a suture extending from the proximal surface through the needle element.

A tissue securing component for gathering tissue of a heart valve leaflet may include at least one elongated support tube having a lumen extending between opposite ends thereof in a longitudinal direction and a suture having a looped portion. At least part of the looped portion may extend through the lumen of the at least one support tube. The tissue securing component maybe adapted to be applied to heart valve leaflet tissue to hold the tissue in a gathered configuration.

The at least one support tube may include first and second support tubes. At least part of the looped portion of the suture may extend through the lumen of each of the support tubes. The support tubes may be adapted to shape the captured tissue into a pleated configuration when the looped portion is tightened around the tissue. Each of the support tubes may have an outer surface having a smooth cylindrical shape. Each of the support tubes may have an outer surface that is roughened or knurled. Each of the support tubes may have an outer surface having serrations. Each support tube may have an outer surface that undulates in a longitudinal direction between opposed ends of the respective support tube. The at least one support tube may consist essentially of one of a metal or a polymer.

The at least one support tube may have a central portion and end portions adjacent the central portion. The central portion may be weaker against bending than the end portions. Each support tube may be adapted to shape the tissue into a pleated configuration when the looped portion is tightened around the tissue. The looped portion of the suture may include a locking sliding knot configured to slide along the suture in only one direction. The tissue securing component may also include a crimp configured to be tightened around the suture when the looped portion of the suture is in a tightened position holding the tissue in the gathered configuration.

A transcatheter method of gathering tissue of a heart valve leaflet may include inserting an elongated catheter assembly to a position adjacent the heart valve leaflet. The catheter assembly may include an outer tube extending in an elongation direction and a capture tool moveable in the outer tube between a contained position and a use position. The method may also include moving the capture tool from the contained position to the use position and manipulating the capture tool so that tissue of the heart valve leaflet is captured by the capture tool. The method may also include retracting the capture tool from the use position toward the contained position to draw the captured tissue into the outer tube in a gathered configuration. The method may also include securing the captured tissue to hold the captured tissue substantially in a pleated configuration by tightening a looped portion of a suture around the captured tissue. At least part of the looped portion may extend through a lumen of at least one support tube.

The at least one support tube may include first and second support tubes. At least part of the looped portion of the suture may extend through the lumen of each of the support tubes. The securing step may include positioning the first and second support tubes on opposite sides of a pleat of the pleated configuration. The securing step may move the looped portion of the suture from an initial position to a tightened position. The support tubes in the initial position may have outer surfaces that are spaced apart from one another and disposed adjacent an inner surface of the outer tube. The support tubes in the tightened position may be disposed on opposite sides of the pleat of the pleated configuration.

The inner surface of the outer tube may have a rib assembly extending therefrom. The rib assembly may form pockets adjacent the inner surface. The looped portion of the suture in the initial position may extend through the pockets of the rib assembly. The securing step may move the looped portion of the suture from the initial position extending within the pockets of the rib assembly to the tightened position out of the pockets of the rib assembly.

The securing step may include tightening a crimp around two portions of the suture after the looped portion of the suture is tightened around the captured tissue. The step of tightening the crimp around the two portions of the suture may include pushing the crimp into a crimping slot to reduce a width of the crimp from an initial width to a tightened width. The crimping slot may have opposed surfaces spaced apart by a distance that is less than the initial width of the crimp.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 1 is a diagrammatic perspective view of the posterior leaflet of a mitral valve;

FIG. 2A is a diagrammatic perspective view of the distal portion of one embodiment of a device for transcatheter gathering of heart valve leaflet tissue, shown with the tissue capture tool omitted for clarity;

FIG. 2B is a longitudinal cross-sectional view of the outer tube and tissue securing component of the device of FIG. 2A, taken along the line 2B-2B of FIG. 2A;

FIG. 3 is a diagrammatic side view of the distal end of the device of FIGS. 2A and 2B, showing the tissue capture tool engaged with the posterior leaflet of the mitral valve of FIG. 1;

FIG. 4A is a diagrammatic perspective view of the tissue securing component of FIGS. 2A and 2B, shown in an expanded condition;

FIG. 4B is a diagrammatic perspective view of the tissue securing component of FIG. 4A, shown in a collapsed condition;

FIG. 5A is a diagrammatic side view of another embodiment of a portion of a tissue securing component for transcatheter gathering of heart valve leaflet tissue;

FIG. 5B is a diagrammatic side view of yet another embodiment of a portion of a tissue securing component for transcatheter gathering of heart valve leaflet tissue;

DETAILED DESCRIPTION

Figure 6:
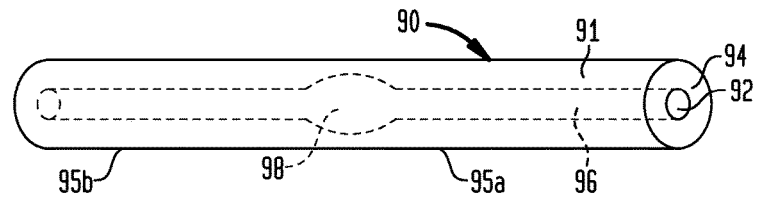
FIG. 6 is a diagrammatic side view of still another embodiment of a portion of a tissue securing component for transcatheter gathering of heart valve leaflet tissue.

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 also has a lower surface 9a and an upper surface 9b. The posterior leaflet 2 has three scalloped portions P1, P2, and P3, any of which may include a portion that is billowed, loose, or floppy, and which therefore may be the cause of a prolapse condition of the valve. The inventive devices, systems, and methods described herein may be adapted to repair such a billowed, loose, or floppy portion of the posterior leaflet 2 or the anterior leaflet 3.

Referring to FIGS. 2A through 4B, an exemplary device 10 for gathering of heart valve leaflet tissue includes an elongated catheter assembly 12 adapted to be inserted through the apex of a human heart so that a distal portion 14 of the catheter assembly may reach the patient's mitral valve 1 for repair thereof.

The catheter assembly 12 includes a containment tube 20 longitudinally slideable within an outer tube 16 between a retracted position within the lumen of the outer tube (FIGS. 2A and 2B) and a deployed position (FIG. 3) in which a distal end 21 of the containment tube protrudes distally beyond the open distal end 17 of the outer tube. The outer tube 16 may be made of one or more echogenic materials, so that the outer tube may be more easily visualized inside a patient using three-dimensional echocardiography.

Referring to FIGS. 2B and 3, the device 10 may include a tissue capture tool in the form of a needle 22 and a resorbable anchor 60. The needle 22 may be longitudinally slideable within the containment tube 20 between a retracted or contained position substantially entirely within the lumen of the containment tube (FIG. 2A), and a deployed or use position in which a tapered distal end 23 of the needle protrudes from the distal end 21 of the containment tube (FIGS. 2B and 3).

The resorbable anchor 60 may initially be stored within the needle 22 and may be deployable therefrom for use. The anchor 60 may have a maximum thickness T between its top surface 61 and bottom surface 62 that is equal to or slightly smaller than the diameter of the lumen of the needle 22. The anchor 60 may be deployed from the needle 22 by increasing the pressure within the needle, using pressurized saline, for example, so that an expelling force applied to the anchor is greater than the frictional forces holding the anchor in place.

An anchor retention member 65 in the form of a wire or suture may be joined substantially to the center of the bottom surface 62 of the anchor 60, such that the anchor can pivot with respect to the retention member. A free end of the retention member 65 may extend proximally through the needle 22, the containment tube 20, and the outer tube 16 to a proximal portion of the device 10 (not shown), where it may be grasped by the user or connected to an actuation mechanism operable by the user. The entire retention member 65 may be adapted to be detached from the anchor 60 when sufficient pulling force is applied by the user after tissue is captured, or the retention member may have a weakened portion near the attachment location with the anchor that is adapted to tear when sufficient pulling force is applied by the user.

The device 10 may optionally include a cutting tube (not shown) for detaching the retention member 65 from the resorbable anchor 60. The cutting tube may be telescopically mounted within the containment tube 20 and around the needle for sliding movement between a retracted position substantially entirely within the lumen of the containment tube, and a deployed position in which a sharpened distal end of the cutting tube protrudes from the distal end 21 of the containment tube. The sharp distal end of the cutting tube may be configured to cut through a portion of the retention member 65, so that the resorbable anchor 60 can be detached from the device 10 and left in a patient.

As shown in FIGS. 2A and 2B, a tissue securing component in the form of a suture loop 32 may be disposed near the open end of the outer tube 16. The suture loop 32 is formed by a length of suture 30 that extends from the proximal end of the device 10 through a suture containment tube 36 that extends longitudinally through the outer tube 16. The suture 30 exits the distal end of the suture containment tube 36 and is threaded around a rib assembly 40 extending circumferentially around and protruding radially inward from an inner surface 42 of the outer tube 16.

Portions of the suture 30 may extend through two support tubes 50a and 50b (collectively support tubes 50). The support tubes 50 each have a lumen 52 extending longitudinally therethrough between opposed ends 54 thereof. Each support tube 50 defines an outer surface 51. As shown for example in FIG. 2A, the outer surface 51 of each support tube 50 has a smooth cylindrical shape, but the outer surface may have other shapes and may not be smooth, as will be described below. Each support tube 50 may be made, for example, of a polymer such as silicone, a metal such as stainless steel or nitinol, or other materials. Each support tube 50 may have sufficient structural rigidity to remain straight or substantially straight when the suture loop 32 is tightened around a captured portion 8 of the posterior leaflet 2, such that the captured portion of the leaflet may form a pleat when the suture loop is tightened, as will be described below.

The rib assembly 40 may be a single rib extending completely around the inner surface 42, or it may include a plurality of spaced apart ribs 40a distributed circumferentially around the inner surface, as shown for example in FIG. 2A. Each rib 40a of the rib assembly 40 has a support surface 44 that projects radially inwardly at an acute angle 48 from the inner surface 42, such that a pocket 46 is defined between the inner surface and the support surface. In any event, as the suture 30 is threaded around the rib assembly 40, it forms a loop 32 near the distal end 17 of the outer tube 16. As shown in FIG. 2A, the support tubes 50 may be disposed between adjacent ones of spaced apart ribs 40a, but that need not be the case. For example, portions of one or more of the support tubes 50 may be disposed in pockets 46 of the rib assembly 40, as long as the frictional force between the support tubes and the ribs is low enough to permit the support tubes to slide off of the ribs when the suture loop 32 is tightened as described below. The suture loop 32 is completed by knotting an end of the suture 30 to an intermediate portion of the suture with a locking sliding knot 34.

The locking sliding knot 34 is configured to slide along the suture 30 in one direction, but not the other. That is, the locking sliding knot 34 can slide in one direction to tighten or reduce the size of the suture loop 32 when the free end of the suture 30 is pulled proximally. However, the locking sliding knot 34 cannot slide in the opposite direction to enlarge the size of the suture loop 32. Thus, by pulling on the free or proximal end of the suture 30, the suture loop 32 is adapted to move from an initial position shown in FIGS. 2A and 4A to a deployed position in which the suture loop is tightened around a captured portion 8 (see FIG. 3) of the posterior leaflet 2. FIG. 4B shows the suture loop 32 in the deployed or tightened position without the captured portion 8 of the posterior leaflet 2. The free or proximal end of the suture 30 is available for grasping by a user at a proximal portion of the device 10 (not shown), where it extends out from the suture containment tube 36. Various specific locking sliding knot designs can be used for the sliding locking knot 34, such as, for example, those shown and described in Eric R. McMillan and Richard B. Caspari, *Arthroscopic knot-tying techniques*, An Atlas of Shoulder Arthroscopy, 81-95 (2003), which is hereby incorporated by reference herein.

A suture cutting tube 38 may be telescopically mounted within the suture containment tube 36 for sliding movement between a retracted position substantially entirely within the lumen of the suture containment tube, and a deployed position in which a distal portion of the suture cutting tube protrudes from the distal end of the suture containment tube. The suture cutting tube 38 may have a sharp distal end 39 that is configured to cut through a portion of the suture 30.

To use the device 10 to gather heart valve leaflet tissue, the suture 30 may be threaded through the suture containment tube 36 and the support tubes 50, and the suture loop 32 may be fitted into the pockets 46 formed by the rib assembly 40, such that the support tubes extend between adjacent ones of the ribs 40a. The support tubes 50a and 50b may be positioned opposite one another along the inner surface 42 of the outer tube 16, as shown in FIG. 2A. A slight proximal tension exerted on the free end of the suture 30 may hold the suture loop 32 in place in the pocket 46 until the suture is deployed by the user.

Next, the distal portion 14 of the catheter assembly 12 may be inserted into a patient, for example, through the apex of the heart into the left ventricle, so that the distal portion is near the mitral valve 1. The distal portion 14 of the catheter assembly 12 may be guided using three-dimensional echocardiography or another imaging technique to visualize the outer tube or other components of the catheter assembly.

The containment tube 20 may then be deployed by sliding the distal portion 21 thereof beyond the distal end 17 of the outer tube 16. The deployed containment tube 20 may be guided such that its distal end 21 contacts the lower surface 9a of the posterior leaflet 2 in a target region thereof to be captured. For example, the target portion of the posterior leaflet 2 to be captured may be a loose edge of the leaflet below the coaption line 5.

Then, the needle 22 may be deployed by sliding the needle distally out of the containment tube 20, such that the tapered distal end 23 of the needle pierces the posterior leaflet 2 and extends therethrough to the upper surface 9b of the leaflet. The anchor 60 may then be deployed from the needle 22 by increasing the pressure within the needle using pressurized saline, for example. With the anchor 60 ejected, the needle 22 may be withdrawn from the posterior leaflet 2 and retracted into the containment tube 20, leaving the anchor adjacent the upper surface 9b of the leaflet and the retention member 65 extending through the opening in the leaflet created by the needle. The retention member 65 may then be pulled proximally by the user until the bottom surface 62 of the anchor 60 contacts the upper surface 9b of the leaflet.

The user may then slide the containment tube 20 proximally to the retracted position within the lumen of the outer tube 16, thereby drawing the anchor 60 proximally, and with it the posterior leaflet 2, until a portion 8 of the posterior leaflet is drawn into the open distal end 17 of the outer tube and through the suture loop 32 (FIG. 2B).

Next, the user may pull the free end of the suture 30 proximally, so that the suture loop 32 and the support tubes 50 will be tightened around the captured portion 8 of the posterior leaflet 2. As the suture 30 is pulled through the locking sliding knot 34, the size of the suture loop 32 will become smaller, causing the suture loop to slide radially inwardly along the support surfaces 44 of the rib assembly 40 until the suture loop leaves the pockets 46 and becomes disengaged from the rib assembly. The free end of the suture 30 may be pulled proximally until the suture loop 32 and the support tubes 50 are fully tightened around the captured portion 8 of the posterior leaflet 2. Each support tube 50 may remain straight or substantially straight when the suture loop 32 is tightened around a captured portion 8 of the posterior leaflet 2, such that the captured portion of the leaflet may form a pleat. Because the suture 30 cannot move in a reverse direction through the locking sliding knot 34, the suture loop 32 is held in the tightened position around the captured portion 8 of the posterior leaflet 2.

With the posterior leaflet 2 ensnared by the suture 30, the suture cutting tube 38 may be moved distally so that the distal portion thereof protrudes from the distal end of the suture containment tube 36. The suture cutting tube 38 may be moved distally until the distal end 39 thereof contacts and cuts through a portion of the suture 30 outside of the suture loop 32 and the locking sliding knot 34.

Next, the retention member 65 may be detached from the anchor 60, for example, by pulling the retention member proximally until at least a portion of the retention member is torn from the anchor. Alternatively, at least a portion of the retention member 65 may be detached from the anchor 60 by cutting the retention member using a cutting mechanism, such as the cutting tube described above. The entire device may then be removed from the patient, and the anchor 60 that is left in the captured tissue of the posterior leaflet 2 may be resorbed over time. The procedure described above may be repeated to apply one or more additional sutures onto the same posterior leaflet 2.

In the foregoing, particular structures have been described that are adapted to gather, secure, and repair heart valve leaflet tissue. The invention also contemplates the use of any alternative structures for such purposes, including structures having different lengths, shapes, and configurations.

For example, as noted above, support tubes having shapes other than that of the support tubes 50 shown above may be used with the device 10, in place of the support tubes shown in FIGS. 2A and 2B. In one variant, FIG. 5A shows a support tube 70 with an outer surface 71 having serrations 76 extending longitudinally between the opposed ends 74 of the support tube. In another variant, FIG. 5B shows a support tube 80 with an outer surface 81 that undulates in a longitudinal direction between the opposed ends 84 of the support tube. The support tube 80 may include a plurality of sections 85, each section extending between two troughs 87 and having a single peak 86 between the troughs.

Such a serrated outer surface 71 or an undulating outer surface 81 may allow the support tubes 70 or 80 to partially embed into a captured portion 8 of a posterior leaflet 2 when the suture loop 32 is tightened. Such outer surface features may permit the support tubes to have an increased surface area of contact between the support tubes and captured tissue compared to support tubes not having such surface features, which may result in increased friction between the support tubes and captured tissue to retain the support tubes on the captured tissue after tightening of the suture loop 32.

The support tubes 70 or 80 may be made of any of the materials described above with reference to the support tubes 50. For example, serrations or an undulating outer surface may be formed in metal support tubes by crimping a cylindrical tube. Serrations or an undulating outer surface may be formed in silicone support tubes by molding the support tube in the desired shape or by chemically etching a cylindrical tube. In additional variations, a metal support tube may have an outer surface that is knurled by a machining process (for a metal support tube). A silicone tube may be roughened by molding a pattern into the outer surface, or by freezing the support tube and then sanding or blasting the outer surface with particles.

In one example, one of the two support tubes 50, 70, or 80 may be used without the other one, such that the suture loop 32 can be tightened around a captured portion 8 of a posterior leaflet 2 with only a single support tube on one side of the captured portion (not shown). Such an embodiment may permit the captured portion 8 of the posterior leaflet 2 to form a pleated structure, or the capture portion may be somewhat pleated, such that the portion of the captured tissue adjacent the support tube is flattened, while the portion adjacent an opposite portion of the suture loop 32 may be bunched or rounded.

In yet another variant, FIG. 6 shows a single support tube 90 that can be used in place of both of the support tubes 50a and 50b shown in FIGS. 2A and 2B. The support tube 90 includes a lumen 92 extending longitudinally therethrough between the opposed ends 94 thereof. The lumen contains narrow portions 96 extending through a first portion 95a and a second portion 95b of the support tube 90, and a widened portion 98 located at the juncture between the first and second portions of the support tube.

The support tube 90 may be weaker against bending in vicinity of the widened portion 98 of the lumen 92 than in the narrow portions 96 of the lumen, so that the support tube can bend at the widened portion, thereby functioning as a living hinge when bent. When a suture loop 32 including the support tube 90 is tightened around a captured portion 8 of a posterior leaflet 2, the first and second portions 95a and 95b may be disposed on opposite sides of the captured portion, thereby forcing the captured portion of tissue into a pleated shape. The support tube 90 may be made of any of the materials described above with reference to the support tubes 50.

The locking sliding knot 34 of the device 10 shown in FIGS. 2A through 4B is only one example of a possible mechanism for fastening the suture loop 32 around a captured portion 8 of a posterior leaflet 2. An alternative embodiment of a device 110 having a suture loop and a crimp adapted to fasten the suture loop around a captured portion 8 of a posterior leaflet 2 is shown in FIGS. 7A-7D.

The device 110 is the same as the device 10 described above, except that the locking sliding knot is replaced by a crimp 134 and a crimping apparatus 140 adapted to fasten the crimp to a tightened suture loop. The crimp 134 is configured to be clamped by the crimping apparatus 140 around two portions of the suture 130 outside the suture loop 132 after the suture loop is tightened around a captured portion 8 of the posterior leaflet 2, such that the suture loop has the deployed or tightened position shown in FIG. 4B.

Figure 7A:
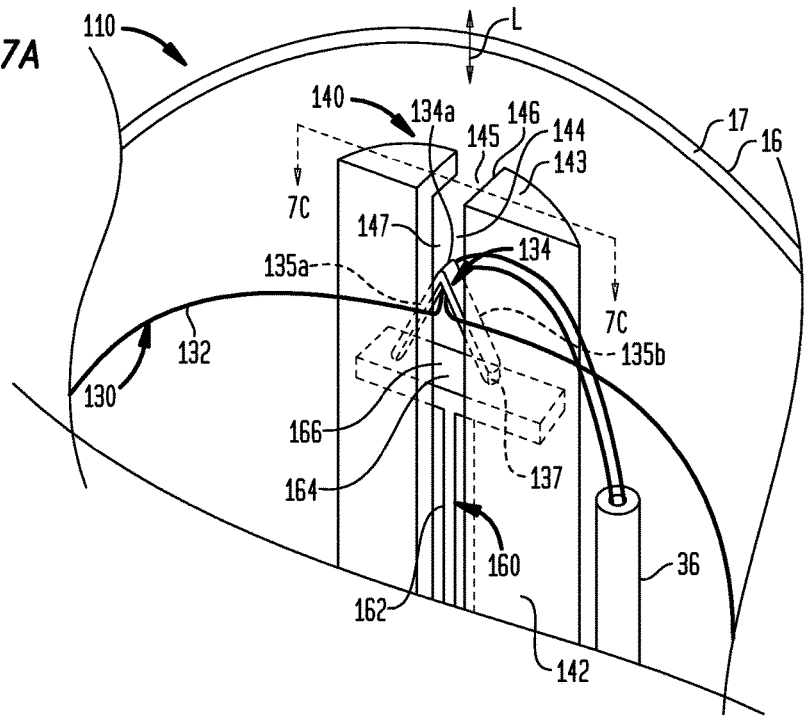
FIG. 7A is a diagrammatic perspective view of the distal portion of another embodiment of a device for transcatheter gathering of heart valve leaflet tissue, shown with a crimp for fastening the tissue securing component.
Figure 7B:
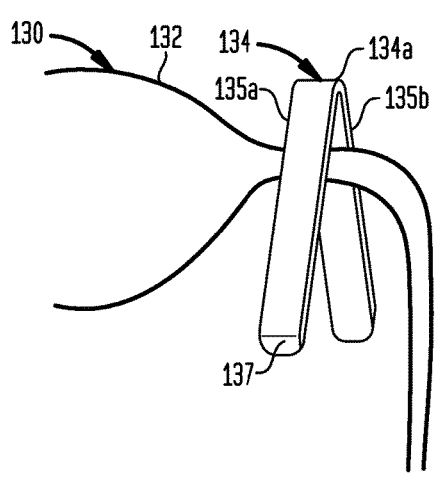
FIG. 7B is a diagrammatic perspective view of the crimp and tissue securing component of FIG. 7A.
Figure 7C:
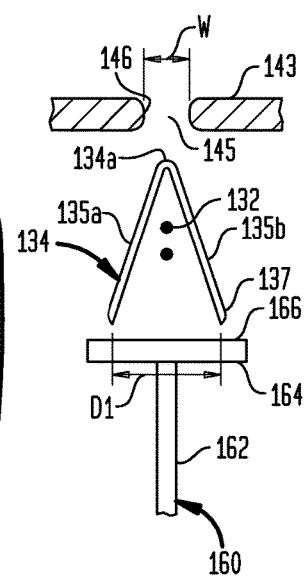
FIG. 7C is a longitudinal cross-sectional view of the crimp and tissue securing component of the device of FIG. 7A, taken along the line 7C-7C of FIG. 7A, shown with the crimp in an open condition.

As shown in FIGS. 7A-7D, the crimp 134 has a V-shaped configuration with two opposed portions 135a and 135b joined to one another at the center 134a of the crimp. The ends 137 of the two opposed portions 135a and 135b are initially spaced apart from one another by a distance D1, as shown in FIG. 7C. As can be seen in FIG. 7C, the distance D1 that initially separates the two opposed portions 135a and 135b is greater than the width W of the crimping slot 145, which will be described below. The crimp 134 may be made of any material that can be permanently deformed to clamp around a portion of the suture loop 132, such as a strip of nitinol or another metal. Similar to the outer surfaces of the support tubes 50, 70, and 80 described above, the two opposed portions 135a and 135b of the crimp may have inwardly-facing surfaces that are roughened, knurled, serrated, or undulating to increase friction between the crimp 134 and the suture 130.

In one example (not shown), the ends 137 may be joined to one another by an additional linking portion of the crimp, such that the crimp is shaped as a continuous loop that may completely encircle the two portions of the suture loop 132 that are to be fastened together, thereby making sure that the suture loop remains in engagement with the crimp throughout the crimping process.

The crimping apparatus 140 includes a plunger 160 and a channel 144 in which the plunger is disposed. The plunger 160 may include an actuation shaft 162 that may extend proximally through the channel 144 and the outer tube 16 to a proximal portion of the device 110 (not shown), where it may be grasped by the user or connected to an actuation mechanism operable by the user. The plunger 160 may also include a pusher plate 164 affixed to a distal end of the actuation shaft 162. The pusher plate 164 may have a contact surface 166 that is oriented substantially perpendicularly to a longitudinal axis L of the outer tube 16.

The channel 144 may be partially enclosed by crimping members 143 and longitudinal members 142 extending proximally from the crimping members along the longitudinal axis L of the outer tube 16. The crimping members 143 may be spaced apart from one another forming the crimping slot 145 that defines the width W (FIG. 7C) between opposed inward-facing surfaces 146 of the crimping members. The longitudinal members 142 may be spaced apart from one another by a longitudinal slot 147 through which portions of the suture 130 may extend.

To use the crimp 134 and the crimping apparatus 140 of the device 110 to secure heart valve leaflet tissue, the suture loop 132 may be threaded through support tubes such as the support tubes 50, 70, 80, or 90 described above, and the suture loop may be fitted into the pockets 46 formed by the rib assembly 40, as described above. The crimp 134 may be placed into the channel 144, with the center 134a oriented facing the crimping slot 145 and the ends 137 abutting the contact surface 166 of the pusher plate 164.

The ends of the suture 130 outside of the suture loop 132 may be threaded into the longitudinal slot 147, between the two opposed portions 135a and 135b of the crimp 134, out of the longitudinal slot, and through the suture containment tube 36, as can be seen in the initial configuration shown in FIG. 7A.

Then, the method described above with respect to the device 10 may be followed until a portion 8 of the posterior leaflet is drawn into the open distal end 17 of the outer tube and through the suture loop 132, similar to the configuration shown in FIG. 2B. Next, the user may pull one or both ends of the suture 130 proximally, so that the suture loop 132 will be tightened around the captured portion 8 of the posterior leaflet 2.

Once the suture loop 32 is fully tightened around the captured portion 8 of the posterior leaflet 2, the user may slide the actuation shaft 162 distally, thereby sliding the center 134a of the crimp 134 distally toward the crimping slot 145. As the actuation shaft 162 moves distally, the center 134a of the crimp 134 extends through the crimping slot 145 until the two opposed portions 135a and 135b of the crimp contact the opposed inward-facing surfaces 146 of the crimping members 143. The contact between the crimping members 143 and the two opposed portions 135a and 135b of the crimp 134 forces the two opposed portions towards one another, so that the opposed portions may deform and bend around the portions of the suture 130 that extend through the crimp.

Figure 7D:
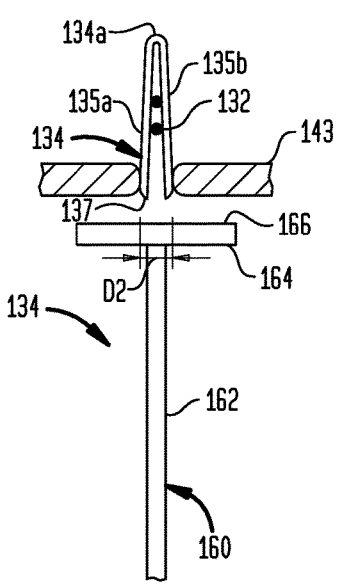
FIG. 7D is a longitudinal cross-sectional view of the crimp and tissue securing component of FIG. 7C, shown with the crimp in a closed condition.

After the opposed portions 135a and 135b of the crimp 134 are bent around the portions of the suture 130, the two opposed portions may be spaced apart from one another by a final distance D2 or less (FIG. 7D). The actuation shaft 162 may continue to slide distally until the contact surface 166 abuts the crimping members 143 and pushes the crimp 134 through the crimping slot 145. In one example (not shown), the contact surface 166 may have a V-shape that is configured such that a raised center portion of the contact surface partially extends into the crimping slot 145, thereby helping to push the crimp 134 completely through the crimping slot when the pusher plate 164 contacts the crimping members 143.

Once the crimp 134 has been secured around the suture 130, thereby holding the suture loop 132 in the tightened position around the captured portion 8 of the posterior leaflet 2, a suture cutting tube (described above) may be moved distally until the distal end thereof contacts and cuts through a portion of the suture 130 outside of the suture loop 132. Finally, the retention member 65 may be detached from the anchor 60, thereby releasing the leaflet 2 from the device 110, and the entire device may then be removed from the patient, as described above.

Although the various gathering devices have been described herein in connection with tightening the posterior leaflet of a mitral valve, all of these devices may be used on other heart valve leaflets, such as the anterior leaflet of the mitral valve, or on any other tissue of the body for which a reduction in the length of the tissue would be beneficial.

Although the invention herein has been described with reference to particular embodiments in which the catheter assembly is inserted into the patient through the apex of the heart (i.e., transapical insertion), it is to be understood that the invention contemplates embodiments in which the catheter assembly extends through a portion of the vasculature of the patient to reach the heart, for example, through a transfemoral or subclavian artery, or using a transseptal procedure. Any other percutaneous technique for accessing the interior of the heart may also be used. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for gathering tissue of a heart valve leaflet, the device comprising:
    an outer tube extending in an elongation direction and having an open distal end, the outer tube having an inner surface and a lumen extending therethrough, the inner surface of the outer tube having a rib assembly extending therefrom, the rib assembly forming pockets adjacent the inner surface;
    a capture tool movable in the outer tube between a contained position and a use position, the capture tool being operable to capture tissue of the heart valve leaflet and to draw the captured tissue into the outer tube in a gathered configuration; and
    a tissue securing component disposed at a distal end of the outer tube and adapted to be applied to the captured tissue to hold the captured tissue in the gathered configuration, the tissue securing component being a suture having a looped portion extending in a single closed curve, at least part of the single closed curve of the looped portion extending through a lumen of each of first and second support tubes,
    wherein the looped portion of the suture is adapted to move from an initial position to a tightened position, the support tubes in the initial position being spaced apart from one another and disposed adjacent the inner surface of the outer tube with the looped portion of the suture extending through the pockets of the rib assembly, the support tubes in the tightened position being disposed opposite one another adjacent the captured tissue.

2. The device of claim 1, wherein the support tubes are adapted to shape the captured tissue into a pleated configuration when the single closed curve of the looped portion is tightened around the captured tissue.

3. The device of claim 2, wherein the support tubes each have an outer surface having a smooth cylindrical shape.

4. The device of claim 2, wherein the support tubes each have an outer surface that is roughened or knurled.

5. The device of claim 2, wherein the support tubes each have an outer surface having serrations.

6. The device of claim 2, wherein each support tube has an outer surface that undulates in a longitudinal direction between opposed ends of the respective support tube.

7. The device of claim 1, wherein the support tube consists essentially of one of a metal or a polymer.

8. The device of claim 1, wherein the rib assembly includes a plurality of spaced apart ribs distributed circumferentially around the inner surface of the outer tube.

9. The device of claim 8, wherein the support tubes in the initial position are disposed between adjacent ones of the spaced apart ribs.

10. The device of claim 1, wherein the rib assembly includes a single continuous rib extending circumferentially around the inner surface of the outer tube.

11. The device of claim 1, wherein the looped portion of the suture includes a locking sliding knot configured to slide along the suture in only one direction.

12. A device for gathering tissue of a heart valve leaflet, the device comprising:
an outer tube extending in an elongation direction and having an open distal end, the outer tube having an inner surface and a lumen extending therethrough;
a capture tool movable in the outer tube between a contained position and a use position, the capture tool being operable to capture tissue of the heart valve leaflet and to draw the captured tissue into the outer tube in a gathered configuration;
a tissue securing component disposed at a distal end of the outer tube and adapted to be applied to the captured tissue to hold the captured tissue in the gathered configuration, the tissue securing component being a suture having a looped portion extending in a single closed curve, at least part of the single closed curve of the looped portion extending through a lumen of at least one support tube;
a crimp configured to be tightened around the suture when the looped portion of the suture is in a tightened position holding the captured tissue in the gathered configuration; and
a crimping apparatus adapted to clamp the crimp around two portions of the suture, the crimping apparatus including a plunger disposed within a channel adjacent an inner surface of the outer tube, the channel being partially defined by crimping members spaced apart from one another by a crimping slot having opposed surfaces spaced apart by a distance that is less than an initial width of the crimp.

13. A device for gathering tissue of a heart valve leaflet, the device comprising:
an outer tube extending in an elongation direction and having an open distal end, the outer tube having an inner surface and a lumen extending therethrough;
a capture tool movable in the outer tube between a contained position and a use position, the capture tool being operable to capture tissue of the heart valve leaflet and to draw the captured tissue into the outer tube in a gathered configuration; and
a tissue securing component disposed at a distal end of the outer tube and adapted to be applied to the captured tissue to hold the captured tissue in the gathered configuration, the tissue securing component being a suture having a looped portion extending in a single closed curve, at least part of the single closed curve of the looped portion extending through a lumen of at least one support tube,
wherein the capture tool includes a needle element and a securing element, the needle element being operable to penetrate tissue of the heart valve leaflet, the securing element having a proximal surface adapted to capture tissue of the heart valve leaflet.

14. The device of claim 13, wherein the securing element includes a resorbable anchor and a suture extending from the proximal surface through the needle element.

15. A tissue securing component for gathering tissue of a heart valve leaflet, the tissue securing component comprising:
at least one elongated support tube having a lumen extending between opposite ends thereof in a longitudinal direction; and
a suture having a looped portion extending in a single closed curve, at least part of the single closed curve of the looped portion extending through the lumen of the at least one support tube,
wherein the tissue securing component is adapted to be applied to heart valve leaflet tissue to hold the tissue in a gathered configuration,
wherein the at least one support tube has a central portion and end portions adjacent the central portion, the central portion being weaker against bending than the end portions, each support tube adapted to shape the tissue into a pleated configuration when the looped portion is tightened around the tissue.

16. The tissue securing component of claim 15, wherein each support tube has an outer surface having a smooth cylindrical shape.

17. The tissue securing component of claim 15, wherein each support tube has an outer surface that is roughened or knurled.

18. The tissue securing component of claim 15, wherein each support tube has an outer surface having serrations.

19. The tissue securing component of claim 15, wherein each support tube has an outer surface that undulates in a longitudinal direction between opposed ends of the respective support tube.

20. The tissue securing component of claim 15, wherein the at least one support tube consists essentially of one of a metal or a polymer.

21. The tissue securing component of claim 15, wherein the looped portion of the suture includes a locking sliding knot configured to slide along the suture in only one direction.

22. The tissue securing component of claim 15, further comprising a crimp configured to be tightened around the suture when the looped portion of the suture is in a tightened position holding the tissue in the gathered configuration.

23. A device for gathering tissue of the heart valve leaflet, the device comprising:
an outer tube extending in an elongation direction and having an open distal end, the outer tube having an inner surface and a lumen extending therethrough;
a capture tool movable in the outer tube between a contained position and a use position, the capture tool being operable to capture tissue of the heart valve leaflet and to draw the captured tissue into the outer tube in a gathered configuration; and
the tissue securing component of claim 20, the tissue securing component disposed at the distal end of the outer tube.

* * * * *